United States Patent [19]

Klotz et al.

[11] Patent Number: 4,499,325

[45] Date of Patent: Feb. 12, 1985

[54] ALKENE CONVERSION USING AMS-1B CRYSTALLINE BOROSILICATE

[75] Inventors: Marvin R. Klotz, Batavia; Edwin F. Peters, Winfield, both of Ill.

[73] Assignee: Standard Oil Company (Indiana), Chicago, Ill.

[21] Appl. No.: 422,743

[22] Filed: Sep. 24, 1982

[51] Int. Cl.$^3$ .............................. C07C 3/20; C07C 5/30
[52] U.S. Cl. ..................................... 585/671; 585/664; 585/312; 585/322; 585/329; 585/415; 585/525; 585/531; 585/670
[58] Field of Search ............... 585/312, 322, 329, 415, 585/417, 418, 419, 510, 520, 525, 531, 664, 666, 670, 671; 252/432

[56] References Cited

U.S. PATENT DOCUMENTS

| | | | |
|---|---|---|---|
| 4,268,420 | 5/1981 | Klotz | 585/641 |
| 4,433,190 | 2/1984 | Sikkenga et al. | 585/660 |
| 4,451,685 | 5/1984 | Nevitt et al. | 585/415 |

*Primary Examiner*—Delbert E. Gantz
*Assistant Examiner*—A. Pal
*Attorney, Agent, or Firm*—Wallace L. Oliver; William T. McClain; William H. Magidson

[57] ABSTRACT

A process to convert an alkene to oligomerized, aromatized and isomerized products comprises contacting such alkene under conversion conditions with an AMS-1B borosilicate catalyst composition.

12 Claims, No Drawings

ALKENE CONVERSION USING AMS-1B CRYSTALLINE BOROSILICATE

BACKGROUND OF THE INVENTION

This invention relates to conversion of alkenes and more particularly relates to conversion of butenes to higher value hydrocarbons using an AMS-1B crystalline borosilicate-based catalyst.

In many instances it is desirable to convert an alkene, such as a butene and $C_2$-$C_3$ olefins, by mechanisms such as oligomerization, structural isomerization, double bond shift, disproportionation and aromatization. Such converted alkenes then can be reacted further such as by polymerization or oxidation to form useful products. Normal alkenes containing four carbon atoms include 1-butene, trans-2-butene and cis-2-butene and are relatively inexpensive feedstocks. Isobutylene is a branched four-carbon alkene useful in the manufacture of polyisobutylenes which can have various properties depending on the manner of polymerization. For example, both crystalline polyisobutylene and viscous polyisobutylene can be manufactured according to well-known processes in the art. In addition, isobutylene is used in the manufacture of methyl-t-butyl ether which is useful as an octane booster in gasoline. Conventionally, butylenes, including isobutylene, are obtained as a by-product from refinery processes such as catalytic or thermal cracking units. For manufacture and uses of butylenes, see Kirk-Othmer, "Encyclopedia of Chemical Technology," Third Edition, Vol. 4, pp. 346-375, incorporated herein by reference.

Aromatic species such as benzene, toluene and xylenes are well-known to have many commercial utilities as chemical feedstocks and in gasoline-grade liquids. $C_5$-$C_{10}$ hydrocarbons are useful as gasoline-grade liquids. A process to convert relatively inexpensive light alkenes to more valuable aromatics and $C_5$-$C_{10}$ hydrocarbons would be very desirable.

Zeolitic materials, both natural and synthetic, are known to have catalytic capabilities for many hydrocarbon processes. Zeolitic materials typically are ordered porous crystalline aluminosilicates having a definite structure with cavities interconnected by channels. The cavities and channels throughout the crystalline material generally are uniform in size allowing selective separation of hydrocarbons. Consequently, these materials in many instances are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

Generally, the term "molecular sieve" includes a wide variety of both natural and synthetic positive-ion-containing crystalline zeolite materials. They generally are characterized as crystalline aluminosilicates which comprise networks of $SiO_4$ and $AlO_4$ tetrahedra in which silicon and aluminum atoms are cross-linked by sharing of oxygen atoms. The negative framework charge resulting from substitution of an aluminum atom for a silicon atom is balanced by positive ions, for example, alkali-metal or alkaline-earth-metal cations, ammonium ions, or hydrogen ions.

Prior art developments have resulted in formation of many synthetic zeolitic crystalline materials. Crystalline aluminosilicates are the most prevalent and, as described in the patent literature and in the published journals, are designated by letters or other convenient symbols. Examples of these materials are Zeolite A (U.S. Pat. No. 2,882,243), Zeolite X (U.S. Pat. No. 2,882,244), Zeolite Y (U.S. Pat. No. 3,130,007), Zeolite ZSM-4 (U.S. Pat. No. 3,578,723), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite NU-1 (U.S. Pat. No. 4,060,590) and others.

Boron is not considered a replacement for aluminum or silicon in a zeolitic composition. However, recently a new crystalline borosilicate molecular sieve AMS-1B with distinctive properties was disclosed in U.S. Pat. Nos. 4,268,420 and 4,269,813 incorporated by reference herein. According to these patents AMS-1B can be synthesized by crystallizing a source of an oxide of silicon, an oxide of boron, an oxide of sodium and an organic template compound such as a tetra-n-propylammonium salt. The process of this invention uses AMS-1B crystalline borosilicate molecular sieve.

Hydrocarbon conversion processes are known using other zeolitic materials. Examples of such processes are dewaxing of oil stock (U.S. Pat. Nos. 3,852,189, 4,221,635 and U.S. Pat. No. Re 28,398); conversion of lower olefins (U.S. Pat. Nos. 3,965,205 and 3,960,978 and European Patent Application 31,675); aromatization of olefins and aliphatics (U.S. Pat. Nos. 3,761,389, 3,813,330, 3,827,867, 3,827,868, 3,843,740, 3,843,741 and 3,914,171); hydrocracking and oligomerization of hydrocarbons (U.S. Pat. Nos. 3,753,891, 3,767,568, 3,770,614 and 4,032,432); conversion of ethane to aromatics and $C_3$+hydrocarbons (U.S. Pat. No. 4,100,218); conversion of straight-chain and slightly branched chain hydrocarbons to olefins (U.S. Pat. Nos. 4,309,275 and 4,309,276); and conversion of $C_4$ paraffins to aromatics (U.S. Pat. No. 4,291,182).

A method to manufacture isobutylene from a linear alkene would be desirable and a method that would isomerize a carbon structure in one step without excessive losses to undesirable by-products would be especially desirable. A process that converts normal butenes to more useful and valuable products such as isobutylene, would be advantageous. Further, a process that could convert linear alkenes to aromatics would be very desirable.

SUMMARY OF THE INVENTION

A process to convert an alkene, to oligomerized, aromatized or isomerized products comprises contacting such alkene under conversion conditions with an AMS-1B borosilicate catalyst composition.

BRIEF DESCRIPTION OF THE INVENTION

This invention is a method to convert a linear alkene, to a mixture containing branched alkenes and aromatics. More particularly, this invention is a method to convert linear butenes to a mixture containing isobutylene, a method to dimerize isobutylene using an AMS-1B borosilicate-based catalyst system and a method to convert butenes to aromatics.

For the purposes of this invention a substantially linear alkene includes linear alkenes, containing two to about eight carbon atoms and at least one carbon-carbon double bond. A preferable substantially linear alkene useful in this invention is a normal butene, including 1-butene, trans-2-butene, and cis-2-butene. Mixtures of substantially linear alkenes can be used in the process of this invention.

The alkenes, or mixtures thereof, used in the process of this invention can be in the presence of other substances such as other hydrocarbon-based molecules. Thus, a feedstream used in the process of this invention comprising a substantially linear alkene also can contain other hydrocarbons such as alkanes, aromatics, hydrogen, and inert gases. A process in which partially reacted hydrocarbons are recycled will contain a mixture including alkanes, alkenes and aromatics. Typically a substantially linear alkene feedstream used in this invention contains about 10 to 100 wt. % substantially linear alkene and preferably contains about 50 to 100 wt. % substantially linear alkene.

In another aspect of this invention, it has been found that addition of water to an alkene feedstock used in a process of this invention alters the end product formed in such process. Specifically, addition of water tends to suppress aromatics formation and thereby yields only aliphatics, typically which are predominantly olefins. In a typical process water may be added in a molar ratio to alkene of about 0.1:1 to 20:1, preferably in a molar ratio of about 1:1 to about 15:1 and most preferably in a molar ratio of about 4:1 to about 12:1.

The catalyst useful in this invention is based on the crystalline borosilicate molecular sieve, AMS-1B, described in U.S. Pat. Nos. 4,268,420 and 4,269,813, incorporated herein by reference.

The catalyst system which is useful in this invention comprises a borosilicate catalyst system based on a molecular sieve material identified as AMS-1B. Details as to the preparation of AMS-1B are described in U.S. Pat. No. 4,269,813. Such AMS-1B crystalline borosilicate generally can be characterized by the X-ray pattern listed in Table I and by the composition formula:

$$0.9 \pm 0.2 M_{2/n}O: B_2O_3: ySiO_2: zH_2O$$

wherein M is at least one cation, n is the valence of the cation, y is between 4 and about 600 and z is between 0 and about 160.

TABLE I

| d-Spacing Å (1) | Assigned Strength (2) |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mole ratios of the various reactants can be varied to produce the crystalline borosilicates of this invention. Specifically, the mole ratios of the initial reactant concentrations are indicated below:

| | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01 | 0.1–2 | 0.1–1 |
| $H_2O/OH^-$ | 10–4000 | 10–500 | 10–500 | wherein R is an organic compound and M is at least one cation having a valence n, such as an alkali metal or an alkaline earth metal cation. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a cation source compound, a boron oxide source, and an organic template compound in water (preferably distilled or deionized). The order of addition usually is not critical although a typical procedure is to dissolve sodium hydroxide and boric acid in water and then add the template compound. Generally, after adjusting the pH, the silicon oxide compound is added with intensive mixing such as that preformed in a Waring Blender. After the pH is checked and adjusted, if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention include silicic acid, sodium silicate, tetraalkyl silicates and Ludox, a stabilized polymer of silicic acid manufactured by E. I. du Pont de Nemours & Co. Typically, the oxide of boron source is boric acid although equivalent species can be used such as sodium borate and other boron-containing compounds.

Cations useful in formation of AMS-1B include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine.

Organic templates useful in preparing AMS-1B crystalline borosilicate include alkylammonium cations or precursors thereof such as tetraalkylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0±0.2 using a compatible base or acid such as sodium bisulfate or sodium hydroxide. After sufficient quantities of silicic acid polymer (Ludox) are added with intensive mixing, preferably the pH is again checked and adjusted to a range of about 11.0±0.2. The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about five to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time. The crystalline material formed can be separated and recovered by well-known means such as filtration with washing. This material can be mildly dried for anywhere from a few hours to a few days at varying temperatures, typically about 25–200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° C. to about 850° C. and preferably about 525° C. to about 600° C. Extreme calcination temperatures or prolonged crystallization times may prove detrimental to the crystal structure or may totally destroy it. Generally there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure by ion exchange, impregnation, a combination thereof, or other suitable contact means. Before placing a catalytically active metal ion or compound on the borosilicate structure, the borosilicate may be in the hydrogen form which, typically, is produced by exchange one or more times with ammonium ion, typically using ammonium acetate, followed by drying and calcination as described above.

The original cation in the AMS-1B crystalline borosilicate, which usually is sodium ion, can be replaced all or in part by ion exchange with other cations including other metal ions and their amine complexes, alkylammonium ions, ammonium ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IVB, VB, VIB, VIIB, and VIII, and rare earth elements.

Groups of elements referred to herein are those contained in the Periodic Table of the Elements, "Handbook of Chemistry and Physics," 54th Edition, CRC Press (1973).

Ion exchange and impregnation techniques are well-known in the art. Typically, an aqueous solution of a cationic species is exchanged one or more times at about 25° C. to about 100° C. A hydrocarbon-soluble metal compound such as a metal carbonyl also can be used to impregnate a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about thirty weight percent, typically from about 0.05 to about 25 weight percent, depending on the process use intended. The optimum amount can be determined easily by routine experimentation.

The AMS-1B crystalline borosilicate useful in this invention typically is admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, alumina sols, hydrated aluminas, clays such as bentonite or kaoline, or other binders well known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere up to 100 wt. % of the total composition. Catalytic compositions can contain about 0.1 wt. % to about 75 wt. % crystalline borosilicate material and preferably contain about 10 wt. % to about 75 wt. % of such material.

Catalytic compositions comprising the crystalline borosilicate material of this invention and a suitable matrix material can be formed by adding a finely-divided crystalline borosilicate and a catalyically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material.

Specific details of catalyst preparations are described in U.S. Pat. No. 4,269,813.

In a process using this invention, a feedstream of an alkene, such as 1-butene, is contacted with a catalytic material containing AMS-1B borosilicate-based catalyst. Generally, in the preferable process of this invention an alkene is contacted with the above-described AMS-1B borosilicate-based catalyst system in the liquid or vapor phase at a suitable reaction temperature, pressure and space velocity. Generally, suitable reaction conditions include a temperature of about 50° C. to about 650° C., a pressure of about 0.1 to about 100 atmospheres (10 to 10,000 kPa) or higher with hydrogen/hydrocarbon ratio of 0 to about 10 or higher at a weight hourly space velocity (WHSV) of about 0.1 to about 40 hr$^{-1}$. In a typical process scheme, a butene-containing hydrocarbon stream is contacted with such catalyst in a reactor at a pressure of about 0.2 to about 50 atmospheres (20 to 5000 kPa) with a hydrogen/butene ratio of 0 to about 10 at a WHSV of about 1 to about 25 hr$^{-1}$. Preferably the butene conversion process of this invention is conducted at about 500° C. to about 600° C. at a pressure of about 1 to about 3 atmospheres (100–300 kPa) with a hydrogen/butene ratio of about 0 to about 6 at a WHSV of about 2 to about 10$^{-1}$.

Preferable temperatures depend in part on the desired products. For example, a temperature of about 65° C. to about 300° C. favors double bond isomerization of alkenes such as interconversion of 1-butene, cis-2-butene and trans-2-butene. A temperature of about 150° C. to about 500° favors skeletal isomerization such as conversion of normal butene to isobutylene. Higher temperatures from about 300° C. to about 650° C. and especially about 370° C. to about 600° C. favor aromatics production.

Certain side reactions such as isobutylene dimerization occur to yield diisobutylene at about 165° C. and higher. Isobutylene can react with an n-butene at about 200° C. to yield a C$_8$ olefin.

The process of this invention can be used to upgrade light ends (C$_1$–C$_4$, H$_2$) from recovered catalytic cracker product to an aromatic naphtha. In another embodiment of the process of this invention butenes can be converted to an aromatic naphtha by a two-stage process in which butenes are contacted in a first reactor containing hydrogen-form AMS-1B crystalline borosilicate, then the light fraction of the resulting product (C$_1$–C$_4$, H$_2$) is contacted in a second reactor with an AMS-1B crystalline borosilicate on which has been placed a Group VIII, Group IB, or Group IIB metal, such as platinum or copper. In such a process the C$_5+$ and C$_1$, C$_2$ and H$_2$ streams are removed and the C$_3$–C$_4$ fraction can be recycled to extinction.

The hydrocarbon feed useful in this invention comprises an alkene containing two to about eight carbon atoms. Also considered an alkene for purposes of this invention is a compound containing a linear alkene segment with four to about ten carbon atoms. The preferable feed contains predominantly linear butene although typically minor amounts of other C$_4$ hydrocarbon as well as lighter components may be present. The hydrocarbon feedstream may be diluted with an inert gas such as nitrogen or helium.

This invention is demonstrated but not limited by the following Examples.

EXAMPLE I

A sample of AMS-1B crystalline borosilicate was prepared by dissolving 120.0 grams of boric acid and 57.0 grams sodium hydroxide in 1,800.0 milliliters of distilled water followed by 282.9 grams of tetrapropylammonium bromide. To this solution, 228.0 grams of Ludox HS-40 were added with vigorous stirring continuing for about 15 minutes after addition. The resulting curdy, gelatinous mixture was placed in a stirred, sealed crystallization vessel to crystallize for seven days. The resulting crystalline material was recovered by filtration, washed thoroughly with distilled water, and dried in a forced draft oven at 165° C. for 16 hours. The dried material was program calcined consisting for four hours from 200° F. (93° C.) to 1,000° F. (538° C.), four hours at 1,000° F. (538° C.), and at least four hours from 1,000° F. (538° C. to 200° F. (93° C.).

Portions of sieve were each exchanged with two times their weight of ammonium acetate in one liter of distilled water at 95° C. for 1.5 hours. The sieve then was filtered, washed with approximately 200 milliliters of distilled water, and filter dried. This procedure was repeated to obtain a total of five ammonium acetate exchanges with the last exchange receiving a wash of about 500 milliliters of water. The washed sieve was dried at 165° C. for approximately 16 hours (overnight). The dried sieve was program calcined with a program consisting of (a) a linear temperature rise of less than or equal to 200° F. per hour from 200° F. to 900° F., (b) holding at 900° F. for 4 hours, and (c) decreasing the temperature at a maximum of 200° F. per hour from 900°F. to 200° F. per hour. Twenty grams of calcined sieve then were exchanged with Ni(NH$_3$)$_6$++ with a solution containing 150 milliliters of 5% Ni(NO$_3$)$_2$·6-H$_2$O in distilled water to which was added approximately 20 milliliters of concentrated ammonium hydroxide. The pH of the exchange solution was 11.6. After exchanging for 2 hours at 90° C., the sieve was filtered from the exchange solution, washed with approximately 300 milliliters of distilled water and dried overnight in the forced draft oven at 165° C. The dried and exchanged sieve was program calcined at 900° F. with the program calcination procedure described above. The catalyst was prepared by dispersing the above calcined and exchanged sieve in PHF-alumina which is initially an acetic acid stabilized alumina hydrosol containing about 8.7% Al$_2$O$_3$. To 21.8 grams of calcined and exchanged sieve were added 23.0 grams of distilled water to fill the sieve pores with water. The wet sieve was then added and thoroughly mixed with 135.0 grams of alumina hydrosol. The mixture was gelled (solidified) with the addition of a solution containing 7.0 milliliters of distilled water and 7.0 milliliters of concentrated ammonium hydroxide. The resulting solid was then dried overnight in a forced air oven at 165° C. The dried solid was program calcined at 900° F. with the program as described above. The calcined solid was crushed and sized to 30 to 80 mesh (U.S. Sieve Series) and recalcined with the above 900° F. program calcination.

Twenty grams of the prepared catalyst was diluted in about 160 grams of 30–50 mesh. Alpha alumina was placed in a one-inch inside diameter 316 stainless steel tube reactor. A 1-butene feed was passed on a once-through operation over the catalyst at 1.3 atmospheres and a weight hourly space velocity (WHSV) of 8.5 hr$^{-1}$. In this example at 206° C. 1-butene was converted 87% by double bond isomerization while at 304° C. total dimerization of C$_4$'s occurred. Analysis of liquid products is shown in Table III.

TABLE I

| | Example 1 | | | |
|---|---|---|---|---|
| Conditions | | | | |
| Average temperature (°C.) | 38 | 73 | 92 | 95 |

TABLE I-continued

| | Example 1 | | | |
|---|---|---|---|---|
| Products (wt. %) | | | | |
| 1-Butene | 99.9 | 96.6 | 96.9 | 97.4 |
| trans-2-Butene | — | 1.6 | 1.5 | 1.2 |
| cis-2-Butene | — | 1.8 | 1.6 | 1.3 |
| Isobutylene | — | — | — | — |
| Other | — | — | — | — |
| Conditions | | | | |
| Average temperature (°C.) | 119 | 147 | 206 | |
| Products (wt. %) | | | | |
| 1-Butene | 91.1 | 63.3 | 12.3 | |
| trans-2-Butene | 4.1 | 16.8 | 39.7 | |
| cis-2-Butene | 4.8 | 18.9 | 37.4 | |
| Isobutylene | — | — | 0.2 | |
| Other | — | 1.0 | 10.3 | |
| Conditions | | | | |
| Average temperature (°C.) | 211 | 236 | 304 | |
| Products (wt. %) | | | | |
| 1-Butene | 12.8 | 11.7 | — | |
| trans-2-Butene | 36.2 | 41.1 | — | |
| cis-2-Butene | 38.9 | 35.7 | — | |
| Isobutylene | 0.2 | 0.2 | — | |
| Other | 11.9 | 11.3 | 100[1] | |

[1] A clear colorless liquid with a 77° C. exotherm.

EXAMPLE II

Isobutylene was converted using the catalyst and procedure described in Example I. Isobutylene was passed through the reactor containing the same catalyst at 5 psig and a WHSV of 5.6. Complete dimerization of isobutylene to liquid product occurred at 126° C. At 279° C. skeletal isomerization was significant and was demonstrated by significant yields of normal butenes. At 335° C. disproportionation to propylene and pentenes is present while some cracking occurs at 384° C. Results are shown in Table II. Anaylsis of liquid products is shown in Table III.

The data show butene skeletal isomerization occurs at about 270° C. to 320° C. and above. Further, normal butenes apparently do not dimerize until skeletal isomerization occurs to form isobutylene after which isobutylene reacts with a normal butene. Since normal butenes are found in product from a conversion using isobutylene as a feed at the same temperatures where dimerization of normal butenes occurs, the skeletal isomerization reaction apparently is reversible above about 270° C.

TABLE II

| | Example II | | | |
|---|---|---|---|---|
| Conditions | | | | |
| Average Temperature (°C.) | 210 | 279 | 335 | 384 |
| Products (wt. %) | | | | |
| 1-Butene | 0.06 | 1.19 | 2.9 | 3.0 |
| trans-2-Butene | 0.37 | 4.05 | 7.1 | 5.9 |
| cis-2-Butene | 0.18 | 2.7 | 7.4 | 9.5 |
| Isobutylene | 94.7 | 51.6 | 17.7 | 12.2 |
| Unknown C$_4$ | — | — | 4.55 | 4.1 |
| Methane | — | — | 0.01 | 0.09 |
| C$_2$ | — | — | 0.56 | 1.9 |
| Propane | — | — | 1.5 | 3.7 |
| Propylene | — | 0.88 | 7.5 | 10.9 |
| C$_5$ | — | — | 26.1 | 21.5 |
| C$_8$ | 4.3 | 37.3 | — | — |
| Paraffin | — | 1.19 | 19.4 | 23.9 |
| Conditions | | | | |
| Average Temperature (°C.) | 432 | 505 | 541 | 589 | 647 |
| Products (wt. %) | | | | | |
| 1-Butene | 3.6 | 4.6 | 5.1 | 7.6 | 7.8 |
| trans-2-Butene | 6.1 | 6.9 | 7.0 | 8.7 | 8.8 |
| cis-2-Butene | 6.8 | 5.2 | 5.4 | 7.1 | 6.6 |
| Isobutylene | 11.4 | 12.3 | 11.9 | 14.8 | 60.9 |
| Unknown C$_4$ | 4.4 | — | — | — | — |
| Methane | 0.4 | 1.2 | 1.6 | 1.8 | 1.6 |
| C$_2$ | 3.6 | 6.6 | 8.5 | 7.8 | 1.2 |
| Propane | 4.8 | 3.9 | 3.4 | 2.6 | 0.2 |
| Propylene | 16.1 | 25.2 | 30.4 | 30.4 | 4.7 |
| C$_5$ | 19.4 | 20.4 | 16.2 | 11.7 | 5.0 |
| C$_8$ | — | — | — | — | — |
| Paraffin | 19.2 | 9.7 | 7.8 | 5.5 | 2.4 |

TABLE III

| Average Reactor Temperature (°C.) | Liquid Product Yield (wt. %) | Aromatic Yield (wt. %) | Xylene Yield (wt. %) | C$_1$-C$_3$ Yield (wt. %) |
|---|---|---|---|---|
| Example I | | | | |
| 236 | 34 | — | — | — |
| 304 | 99 | — | — | — |
| 397 | 98 | — | — | — |
| 436 | 51 | — | — | — |
| 485 | 27 | 19.0 | 8.2 | — |
| 532 | 27 | 21.0 | 9.9 | — |
| Example II | | | | |
| 41 | 0 | — | — | — |
| 142 | 93 | — | — | — |
| 162 | 73 | — | — | — |
| 211 | 55 | — | — | — |
| 279 | 97 | — | — | — |
| 335 | 99 | 1 | — | 0.1 |
| 384 | 69 | 6.1 | 2.4 | 5.1 |
| 432 | 50 | 10.3 | 4.2 | 12.4 |
| 505 | 28 | 11.3 | 4.8 | 26.6 |
| 540 | 23 | 14.5 | 7.8 | 33.8 |
| 589 | 14 | 10.9 | 4.8 | 36.6 |
| 647 | 3 | 2.1 | 1.0 | 7.5 |

EXAMPLE III

A sample of AMS-1B crystalline borosilicate was prepared by dissolving 11,000.0 grams of boric acid and 380.0 grams sodium hydroxide in 550.0 milliliters of distilled water followed by 850.0 grams of tetrapropylammonium bromide. To this solution, 3,375.0 grams of Ludox HS-40 were added with vigorous stirring continuing for about 15 minutes after addition. The resulting curdy, gelatinous mixture was placed in a stirred, sealed crystallization vessel to crystallize for six days at 145° C. The resulting crystalline material was recovered by filtration, washed thoroughly with distilled water, and dried in a forced draft oven at 165° C. for 16 hours. The dried material was program calcined consisting for four hours from 200° F. (93° C.) to 1,000° F. (538° C.), four hours at 1,000° F. (538° C.), and at least four hours from 1,000° F. (538° C.) to 200° F. (93° C.).

One hundred grams of sieve were exchanged with 100 grams of ammomium acetate in one liter of distilled water at 95° C. for 1.5 hours. The sieve then was filtered, washed with approximately 200 milliliters of distilled water, and filter dried. This procedure was repeated to obtain a total of five ammonium acetate exchanges with the last exchange receiving a wash of about 500 milliliters of water. The washed sieve was dried at 165° C. for approximately 16 hours (overnight). The dried sieve was program calcined with a program consisting of (a) a linear temperature rise of less than or equal to 200° F. per hour from 200° F. to 900° F., (b)

holding at 900° F. for 4 hours, and (c) decreasing the temperature at a maximum of 200° F. per hour from 900° F. to 200° F. per hour. The calcined sieve then was exchanged with a solution containing 1,500 milliliters of 5% of $Ni(NO_3)_2 \cdot 6H_2O$ in distilled water. After exchanging for 2 hours at 90° C., the sieve was filtered from the exchange solution, washed with approximately 300 milliliters of distilled water and dried overnight in the forced draft oven at 165° C. The dried and exchanged sieve was program calcined at 900° F. with the program calcination procedure described above. The catalyst was prepared by dispersing the above calcined and exchanged sieve in PHF-alumina which is initially an acetic acid stabilized alumina hydrosol containing about 8.7% $Al_2O_3$. To 109 grams of calcined and exchanged sieve were added 121 grams of distilled water to fill the sieve pores with water. The wet sieve was then added and thoroughly mixed with 675 grams of alumina hydrosol. The mixture was gelled (solidified) with the addition of a solution containing 40 milliliters of distilled water and 40 milliliters of concentrated ammonium hydroxide. The resulting solid was then dried overnight in a forced air oven at 165° C. The dried solid was program calcined at 900° F. with the program as described above. The calcined solid was crushed and sized to 30 to 50 mesh (U.S. Sieve Series) and recalcined with the above 900° F. program calcination.

Twenty grams of the prepared 30–50 mesh catalyst were diluted with 162 grams of alpha alumina and placed in a one-inch inside diameter 316 stainless steel tube reactor. The reactor was pumped full and pressurized to 450 psig with distilled water with the water passing through the reactor in an upward flow manner. After pressurization with water, propylene or ethylene was pumped simultaneously through the reactor. The results for propylene are shown in Table IV. Reaction with ethylene gave the same distribution of carbon numbers but different isomer distribution within each carbon number grouping.

TABLE IV

| | Example III | | | |
|---|---|---|---|---|
| Temperature (°C.)[1] | 363 | 395 | 435 | 384 |
| Propylene WHSV (hr$^{-1}$) | 2.10 | 1.96 | 2.12 | 2.12 |
| H$_2$O/Propylene (molar ratio) | 4.05 | 3.68 | 3.66 | 3.37 |
| Propylene Conversion to Aliphatics (wt. %) | 96 | 94 | 92 | 97 |
| Propylene Converted to Light Gases (wt. %) | 11 | 22 | 28 | 10 |
| Propylene Converted to C$_5$-C$_{11}$ oligomers (wt. %) | 85 | 72 | 64 | 87 |

TABLE IV-continued

| | Example III | | |
|---|---|---|---|
| Temperature (°C.)[1] | 378 | 391 | 430 |
| Propylene WHSV (hr$^{-1}$) | 2.13 | 2.12 | 2.13 |
| H$_2$O/Propylene (molar ratio) | 3.64 | 6.60 | 9.85 |
| Propylene Conversion to Aliphatics (wt. %) | 98 | 96 | 84 |
| Propylene Converted to Light Gases (wt. %)[2] | 17 | 18 | 7 |
| Propylene Converted to C$_5$-C$_{11}$ oligomers (wt. %) | 81 | 78 | 77 |

[1] Measured as highest temperature along the catalyst bed.
[2] $C_1$, $C_2$ and $C_4$ hydrocarbons.

What is claimed is:

1. A process to convert a substantially linear alkene to isomerized products comprising contacting such alkene under conversion conditions with an AMS-1B crystalline borosilicate-based catalyst composition.
2. The process of claim 1 wherein the alkene comprises a normal alkene having two to about eight carbon atoms.
3. The process of claim 1 wherein the alkene is a butene.
4. The process of claim 3 wherein the butene is a normal butene.
5. The process of claim 3 wherein the butene is isobutylene.
6. The process of claim 3 wherein the alkene is 1-butene.
7. The process of claim 1 wherein the AMS-1B crystalline borosilicate composition is incorporated within an alumina or silica-alumina matrix.
8. The process of claim 1 wherein butene is converted with catalyst comprising AMS-1B crystalline borosilicate incorporated within an alumina matrix, and exchanged or impregnated with an ion or molecule of nickel, at a temperature of about 50 to about 650° C. at a pressure of about 0.2 to about 50 atmospheres with a hydrogen/butene molar ratio of 0 to about 10 at a WHSV of about 1 to about 25 hr$^{-1}$.
9. The process of claim 1 wherein alkene is ethylene or propylene.
10. The process of claim 1 wherein water is added to a feed stock containing the alkene in a molar ratio of water to alkene of about 0.1:1 to about 20:1.
11. The process of claim 10 wherein the molar ratio of water to alkene is about 1:1 to about 15:1.
12. The process of claim 10 wherein the molar ratio of water to alkene is about 4:1 to about 12:1.

* * * * *

UNITED STATES PATENT OFFICE
CERTIFICATE OF CORRECTION

Patent No. 4,499,325            Dated February 12, 1985

Inventor(s) MARVIN R. KLOTZ - EDWIN F. PETERS

It is certified that error appears in the above-identified patent and that said Letters Patent are hereby corrected as shown below:

| Patent Column | Line | | |
|---|---|---|---|
| 7 | 20 | "$10^{-1}$" should be | -- $10\ hr^{-1}$ -- |

Signed and Sealed this

Twenty-sixth Day of November 1985

[SEAL]

Attest:

DONALD J. QUIGG

Attesting Officer      Commissioner of Patents and Trademarks